(12) United States Patent
Stephenson

(10) Patent No.: US 10,709,313 B2
(45) Date of Patent: Jul. 14, 2020

(54) SURGICAL INSTRUMENT INSPECTION SYSTEM

(71) Applicant: SP Concepts, Inc., Coon Rapids, MN (US)

(72) Inventor: Kevin L. Stephenson, Coon Rapids, MN (US)

(73) Assignee: NCI, Inc., Minneapolis, MN (US)

(*) Notice: Subject to any disclaimer, the term of this patent is extended or adjusted under 35 U.S.C. 154(b) by 320 days.

(21) Appl. No.: 15/711,686

(22) Filed: Sep. 21, 2017

(65) Prior Publication Data

US 2018/0084162 A1 Mar. 22, 2018

Related U.S. Application Data

(60) Provisional application No. 62/397,516, filed on Sep. 21, 2016.

(51) Int. Cl.
*A61B 1/00* (2006.01)
*B08B 9/043* (2006.01)
(Continued)

(52) U.S. Cl.
CPC ...... *A61B 1/00124* (2013.01); *A61B 1/00045* (2013.01); *A61B 1/00105* (2013.01);
(Continued)

(58) Field of Classification Search
CPC .............. H04N 5/2252; A61B 1/00045; A61B 1/00105; A61B 1/00108; A61B 1/00124; A61B 1/122; G02B 23/2476
See application file for complete search history.

(56) References Cited

U.S. PATENT DOCUMENTS

| 5,003,998 A | 4/1991 | Collett |
| 5,168,593 A | 12/1992 | Poje et al. |

(Continued)

FOREIGN PATENT DOCUMENTS

| JP | H01179119 A | 7/1989 |
| JP | 2008-173399 A | 7/2008 |

(Continued)

OTHER PUBLICATIONS

Aug. 23, 2016 Amazon.com: Android Smartphone USB Endoscope 3.0 MP CMOS HD Borescope Waterproof Inspection Camera Snake Camera for Samsung Galaxy/ . . . https://www.amazon.com/dp/B01IR6D1EK?psc=1; 6 pgs.

(Continued)

*Primary Examiner* — Aaron B Fairchild
(74) *Attorney, Agent, or Firm* — Dicke, Billig & Czaja, PLLC

(57) ABSTRACT

An inspection system for inspecting a surgical instrument lumen at a cleaning station. The system includes a waterproof housing and a waterproof borescope assembly. The housing carries an image processor electronically connected to a display screen, and provides an imaging port. The borescope assembly includes a borescope, an image sensor and a connector assembly. The connector assembly is configured to selectively connect with the imaging port. When connected, signals from the image sensor are delivered to the image processor. A cleaning implement (e.g., wipe) is optionally provided with the borescope. During a cleaning operation, the inspection system is located in close proximity to cleaning liquid, affording the operator the ability to inspect lumen(s) of the surgical instrument throughout the cleaning operation without fear of damaging the inspection system. The borescope assembly can be disconnected from the housing and repeatedly sterilized or disinfected.

19 Claims, 5 Drawing Sheets

(51) Int. Cl.
*H04N 7/10* (2006.01)
*A61B 1/06* (2006.01)
*A61B 1/05* (2006.01)
*A61B 1/12* (2006.01)
*A61B 1/04* (2006.01)
*A61L 2/26* (2006.01)
*A61L 2/14* (2006.01)
*H04N 5/374* (2011.01)
*H04N 5/225* (2006.01)

(52) U.S. Cl.
CPC .......... *A61B 1/00126* (2013.01); *A61B 1/042* (2013.01); *A61B 1/05* (2013.01); *A61B 1/0661* (2013.01); *A61B 1/123* (2013.01); *A61L 2/26* (2013.01); *B08B 9/0436* (2013.01); *H04N 7/10* (2013.01); *A61B 1/122* (2013.01); *A61L 2/14* (2013.01); *A61L 2202/24* (2013.01); *H04N 5/2256* (2013.01); *H04N 5/374* (2013.01); *H04N 2005/2255* (2013.01)

(56) References Cited

U.S. PATENT DOCUMENTS

| | | | |
|---|---|---|---|
| 5,297,310 A | | 3/1994 | Cox et al. |
| 5,795,404 A | | 8/1998 | Murphy et al. |
| 5,832,584 A | | 11/1998 | Folino et al. |
| 5,873,814 A | * | 2/1999 | Adair ................. A61B 1/00039 348/65 |
| 5,951,463 A | | 9/1999 | Lombardi et al. |
| 7,979,943 B2 | | 7/2011 | Arai et al. |
| 8,189,043 B2 | | 5/2012 | Schneider et al. |
| 9,296,024 B2 | | 3/2016 | Sweeney |
| 2004/0187892 A1 | * | 9/2004 | Maguire, Jr. ............ A46B 3/18 134/8 |
| 2007/0251039 A1 | | 11/2007 | Kobayashi et al. |
| 2008/0195128 A1 | * | 8/2008 | Orbay ................ A61B 1/00048 606/170 |
| 2009/0225159 A1 | * | 9/2009 | Schneider .......... A61B 1/00124 348/82 |
| 2013/0090527 A1 | | 4/2013 | Axon |
| 2014/0063228 A1 | | 3/2014 | Boles et al. |

FOREIGN PATENT DOCUMENTS

| | | |
|---|---|---|
| JP | 2009-172056 A | 8/2009 |
| JP | 4390518 B2 | 12/2009 |

OTHER PUBLICATIONS

Aug. 23, 2016 Lyman Products Your Primary Source for Reloading Equipment; http://www.lymanproducts.com/lyman/GunCleaning/borescope.php; 2 pgs.

Aug. 23, 2016 EconoLed 10M 30ft USB Waterproof Endoscope Borescope Inspection Camera Pibe Locator: Amazon.com Industrial & Scientific; https://www.amazon.com/EconoLedWaterproofEndoscopeBorescopeInspection/dp/B00V8A6CSU; 7 pgs.

General® Pipe & Duct Inspection Probe & Reel Set, User's Manual, P16PIP; Mar. 27, 2012; 16 pgs.

* cited by examiner

SURGICAL INSTRUMENT INSPECTION SYSTEM

CROSS-REFERENCE TO RELATED APPLICATIONS

This Non-Provisional Patent Application claims the benefit of the filing date of U.S. Provisional Patent Application Ser. No. 62/397,516, filed Sep. 21, 2016, entitled "Surgical Instrument Inspection System," the entire teachings of which are incorporated herein by reference.

BACKGROUND

The present disclosure relates to the inspection of surgical instrument lumen(s). More particularly, it relates to systems for inspection systems appropriate for use with the cleaning of a surgical instrument lumen, such as an endoscope lumen or channel, in a liquid (e.g., water) environment.

A plethora of different surgical instruments incorporate a tubular design in which one or more lumens or channels are utilized to facilitate caregiver interface with a target site inside the patient's body. For example, irrigation, suction, additional instrument(s), etc., are commonly delivered to an internal treatment site via the lumen(s) of a surgical instrument. Endoscopes are but one example of a surgical instrument providing at least one lumen (sometimes referred to as a "channel" in the context of endoscopes).

Regardless of exact form, under circumstances where the particular surgical instrument is intended and designed for repeated use, the instrument must be sterilized or high level disinfected prior to each use. Prior to the sterilization or high level disinfection, all debris and foreign matter must be removed from all surfaces of the instrument, both inside and out. In other words, the internal surfaces of the surgical instrument otherwise defining the instrument's lumen(s) must be cleaned.

Currently, the process after a procedure to clean a surgical instrument starts in the operating field. A surgical technician wipes the outside of the surgical instrument and flushes out the lumen(s) with sterile water or enzymatic solution (depending upon the procedure for which the surgical instrument was used). The next step is to manually clean the surgical instrument with an enzymatic solution in a decontamination or reprocessing area of the caregiver's facility. This process is performed at a sink filled with enzymatic solution. To clean surgical instrument lumen(s) (e.g., the lumen(s) or channel(s) of an endoscope), a technician inserts a brush into the lumen while submersed in the enzymatic solution. The technician manipulates the brush with back-and-forth and twisting motions, scrubbing debris and residue from the internal surfaces. With sufficient time and effort, this traditional cleaning technique can be effective in removing all debris from the lumen surfaces. However, the technician has no way of knowing in advance the time and effort required for a particular cleaning task as the physical constraints and type(s) of debris encountered vary widely. Moreover, because the lumen surfaces are internal or "hidden" relative to an exterior of an otherwise non-transparent surgical instrument (e.g., typically formed of surgical grade stainless steel or the like), the technician has no way of visually evaluating cleanliness of the lumen surfaces with the naked eye. It is exceedingly difficult to fully clean what the technician cannot see. An additional concern with traditional brush cleaning is that bristles of the brush may detach from the cleaning tool and problematically become lodged within the lumen.

Multiple surveys and clinical evaluations have documented that surgical instrument lumens (such as endoscopic channels) are still not fully clean following traditional cleaning. Most have reported that 60%-100% of lumens are still dirty when inspected following a traditional cleaning process.

Inspection tools are available for inspecting the surgical instrument lumen(s) following cleaning, and are generally in the form of a small diameter borescope.

While useful for evaluating cleaning efforts well after the technician has completed cleaning, borescope systems and complementary small diameter (2 mm or less) metal-oxide-semiconductor (CMOS) borescope systems promoted for surgical instrument inspection cannot be used at or during the time of cleaning due to the presence of liquid. Further, conventional CMOS borescope systems cannot be sterilized in a low temperature gas plasma sterilizer or high level disinfected.

SUMMARY

The inventor of the present disclosure recognized that a need exists for systems and methods that address one or more of the above problems.

Some aspects of the present disclosure are directed toward a surgical instrument lumen inspection system for inspecting a lumen of a surgical instrument at a cleaning station. The inspection system includes a waterproof housing and a waterproof borescope assembly. The housing carries an image processor electronically connected to a display screen, and provides an imaging port. The borescope assembly includes a borescope, an image sensor and a connector assembly. The connector assembly is configured to selectively connect to the imaging port. Upon connection, signals generated by the image sensor are delivered to the image processor. An illumination source is optionally carried by the housing; with these and relative embodiments, the illumination source is selectively connected to the borescope assembly, providing desired light during borescope operation. Images and videos generated during borescope operation and captured by the image sensor (e.g., a CMOS sensor) are electronically signaled to the display screen for viewing by an operator. In some embodiments, a cleaning implement (e.g., cloth wipe) is provided with, or carried by, the borescope.

During a surgical instrument cleaning operation, the surgical instrument undergoing cleaning is repeatedly subjected to washing operations using liquid (e.g., enzymatic solution) held in a sink of the cleaning station. The inspection system is located in close proximity to the sink (and thus the liquid), affording the operator the ability to inspect lumen(s) of the surgical instrument throughout the cleaning operation without fear of damaging the inspection system. In some optional embodiments, the cleaning implement carried by the borescope is utilized to effectuate cleaning or scrubbing of the surgical instrument lumen(s).

Using a small diameter waterproof borescope at the time of cleaning at the sink, allows the technician to observe their cleaning process for the first time. In some optional embodiments, to make it easy for the technician to clean the lumens and channels, a cleaning pad can be attached to the borescope toward the distal end to wipe all foreign matter off of the interior walls that they see with the borescope in the surgical instrument lumens and endoscopic channels. With these optional embodiments, there are no potential bristles that can be left behind.

After a surgical instrument cleaning operation, the inspection system may need to be cleaned, sterilized, and/or high level disinfected before repeated use. In some embodiments, the borescope assembly can be entirely disconnected from the housing and repeatedly subjected to low-temperature, hydrogen peroxide gas plasma sterilization and/or high level disinfection without damaging components of the borescope assembly.

DETAILED DESCRIPTION

Figure 1:
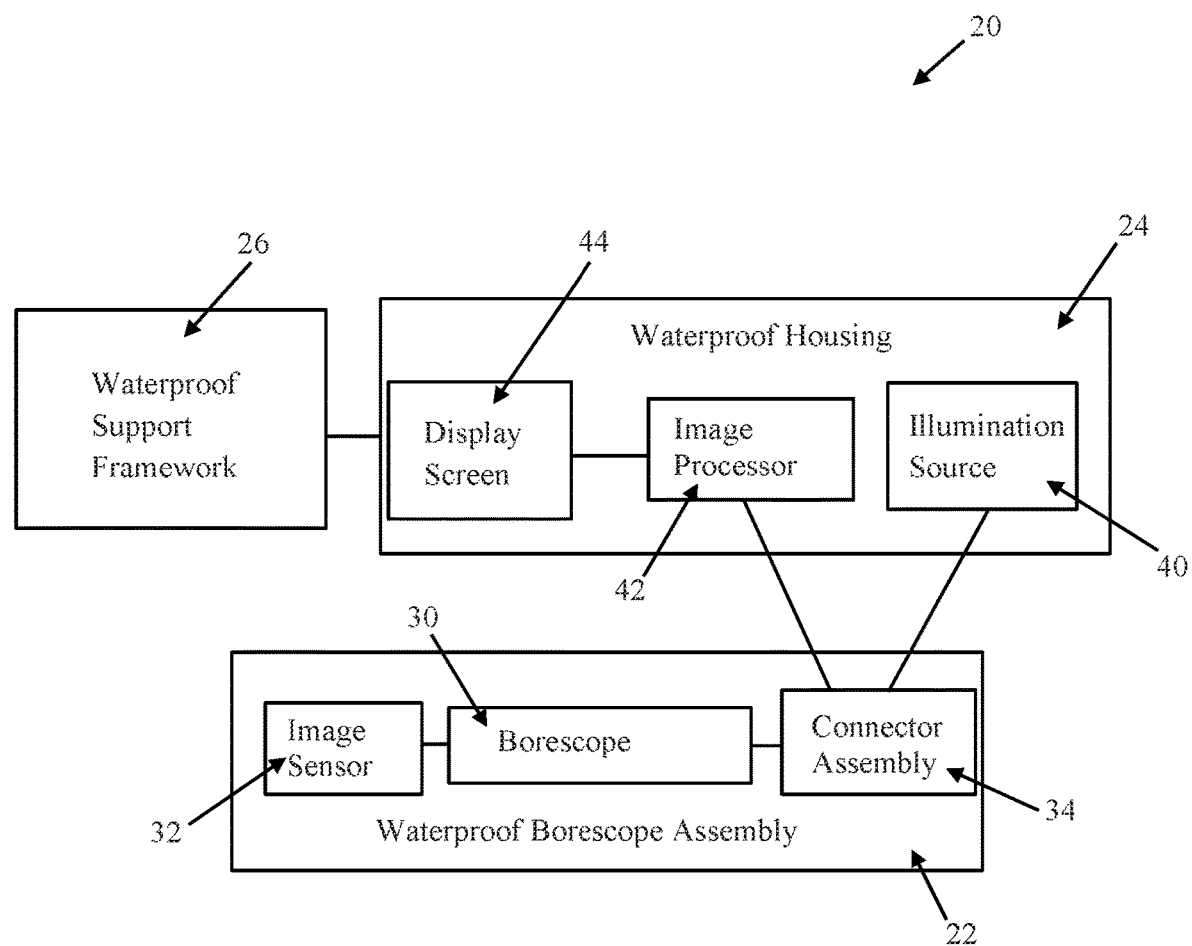
FIG. 1 is a block diagram of an inspection system in accordance with principles of the present disclosure.

One embodiment of a surgical instrument inspection system 20 in accordance with principles of the present disclosure in shown in block form in FIG. 1. The inspection system 20 is configured for use in wet cleaning environments, and in particular during, or as part of, a surgical instrument lumen cleaning process. The inspection system includes a waterproof borescope assembly 22, a waterproof housing 24, and an optional waterproof support framework 26. Details on the various components are provided below. In general terms, the borescope assembly 22 includes a waterproof borescope 30, an image sensor 32, and a connector assembly 34. The housing maintains an illumination source 40, an image processor 42, and a display screen 44. The illumination source 40 is connected to the borescope 30 via the connector assembly 34, and is operable to provide necessary or desired light for viewing with the borescope 30. In other embodiments, the illumination source 40 can be carried by the borescope 30. The image processor 42 is connected to the image sensor 32 through the borescope 30 via the connector assembly 34, and is electronically connected to the display screen 44 for displaying images and/or videos generated at the borescope 30 on the display screen 44. The support framework 26, where provided, includes one or more components that support the housing 24 and/or the borescope 40 (either separate from one another or in tandem) at the surgical instrument cleaning station. By providing each of the components 22-26 in a waterproof format, the inspection system 20 can be located or installed at the surgical instrument cleaning station (e.g., immediately adjacent a sink in which a surgical instrument will be cleaned), and used by a technician at any time during a surgical instrument cleaning process to inspect or evaluate cleanliness of lumen(s)). Further, a detachable connection is established between the borescope assembly 22 and the housing 24 in some embodiments (e.g., via the connector assembly 34), with the borescope assembly 22 being configured for repeated sterilization when disconnected from the housing 24. In some optional embodiments, the inspection systems of the present disclosure are configured to additionally provide lumen cleaning features, such as a cleaning implement carried by the borescope 30.

In some embodiments, the inspection systems of the present disclosure utilize CMOS imaging or sensing camera technologies. With this in mind, and with reference to FIG. 2, the waterproof borescope assembly 22 can assume various forms. In some embodiments, the borescope 30, the image sensor 32 (hidden in FIG. 2) and the connector assembly 34 are provided as single device, with the connector assembly 34 providing selective connection between the image sensor 32 and the image processor 42 (FIG. 1) in establishing a "camera"; in other embodiments, a more complete camera can be integrally attached to the borescope 30. The waterproof borescopes 30 of the present disclosure generally include a guide tube 50 and a sheath 52 (or other waterproofing construction). The guide tube 50 can have a flexible construction as is known in the art, and carries a relay system (not shown) by which an image (or signal representative of an image) at a distal tip (or objective end) 54 of the guide tube 50 is delivered or relayed. In some embodiments, for example, the image sensor 32 (hidden in FIG. 2), such as a CMOS sensor, is carried at the distal tip 54. Further, the guide tube 50 incorporates or carries various optical components (e.g., fiber optics, light guides, etc.) for delivering light to the distal tip 54 (and illuminating the area to be observed at the distal tip 54) as described in greater detail below.

The guide tube 50 can have a relatively small outer diameter, for example on the order of 2 mm in some non-limiting embodiments. In some embodiments, while a majority of the guide tube 50 has the flexible construction as described above, a distal segment 56 (including the distal tip 54) can have a more rigid construction. A length of the rigid distal segment can be on the order of 2-10 mm in some non-limiting embodiments. In other embodiments, an entirety of the guide tube 50 can be flexible.

In some embodiments, the sheath 52 extends along an exterior of the guide tube 50, serving to render the borescope 30 waterproof (i.e., impervious to surgical instrument cleaning solutions, allowing the borescope 30 to be submersed in a cleaning solution without damage). The sheath 52 can be a thin, water impermeable polymer material tubing applied over the guide tube 50, a water impermeable coating applied to the guide tube 50, or have any other construction that effectuates a water-tight seal to the optical relay system components (not shown) carried within the guide tube 50. In addition, the sheath 52 may render the borescope 30 to be sterilizable (e.g., able to be repeatedly low-temperature, hydrogen peroxide gas plasma sterilized or high level disinfected without damaging any components of the borescope 30). In other embodiments, the guide tube 50 can be a waterproof sheathing, such that a separate or additional sheath is not required. For example, in some non-limiting embodiments, the sheath 52 and/or the guide tube 50 is formed of a thermoplastic elastomer such as a polyether block amide (e.g., PEBAX® available from Arkema). Regardless, the image sensor 32 (e.g., CMOS sensor) is maintained proximate the distal end 54, with the borescope 30 established a water tight seal about the image sensor 32 relative to the distal end 54. For example, the image sensor 34 can be bonded or adhered to the borescope 30 (e.g., where the borescope 30 comprises a waterproof sheathing as described above), along with a lens or similar structure that further protects the image sensor 32 from the environment external the borescope 30 at the distal end 54. In some embodiments, the borescope 30 can include one or more additional features or components that promote a waterproof construction, such as watertight seals, etc.

Figure 3:
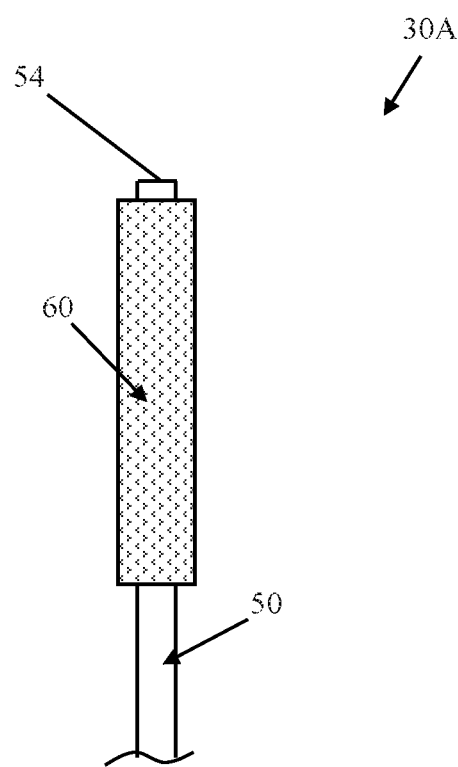
FIG. 3 is a simplified side view of a portion of an alternative borescope useful with systems of the present disclosure.

In some optional embodiments, a cleaning implement is formed or carried by the guide tube 50 in close proximity to the distal tip 54. For example, FIG. 3 illustrates a portion of an alternative waterproof borescope 30A in accordance with principles of the present disclosure. The borescope 30A can be highly akin to the descriptions above, and includes the guide tube 50 terminating at the distal tip 54. In addition, the borescope 30A includes a cleaning implement 60. The cleaning implement 60 is attached to and radially projects from an exterior of the guide tube 50 proximate the distal tip 54, and can be a cloth wipe, such as a microfiber cloth wipe, wrapped about the borescope 30A. A construction of the cloth wipe can assume various forms appropriate for cleaning or scrubbing typical surgical residue from internal surfaces of a surgical instrument. As compared to brushes conventionally employed with surgical instrument lumen cleaning tools, the optional cloth wipe is atraumatic to the interior surface of the lumen (or channel) that is being cleaned; it not only dislodges debris from the surface, but serves to capture the dislodged foreign material. Exemplary formats of the cloth wipe include, but are not limited to, microfiber, foam, nylon and silicone. With embodiments in which the cleaning implement 60 is a cloth wipe, the cloth wipe 60 can be connected to the guide tube 50 in various manners. For example, in some embodiments, an adhesive (e.g., pressure sensitive adhesive) is employed. The cleaning implement 60 can assume a variety of forms differing from a cloth wipe, such as a bristle-type brush conventionally used with surgical instrument lumen cleaning tools.

Returning to FIG. 2, the connector assembly 34 is generally configured to be repeatedly sterilizable (e.g., able to be repeatedly low-temperature, hydrogen peroxide gas plasma sterilized and/or high level disinfected without damaging any components of the connector assembly 34), and can have a bifurcated construction. In some embodiments, the connector assembly 34 includes an illumination plug 70, an illumination cable 72, an imaging plug 74, an illumination cable 76, a bifurcation joint 78, and a strain relief body 80. The illumination plug 70 is configured for selective connection to a port provided with the housing 24 (FIG. 1) as described in greater detail below, and can incorporate features effecting a water tight seal when secured to the port. Further, the illumination plug 70 incorporates electrical and/or optical components appropriate for delivering light received from the illumination source 40 (FIG. 1) to the illumination cable 72. The illumination cable 72, in turn, is appropriately configured for delivering received light to the borescope 40. The illumination plug 70 and corresponding cable 72 are configured to be repeatedly sterilizable as described above.

The imaging plug 74 is also configured for selective connection to a port provided with the housing 24 (FIG. 1) as described in greater detail below, and can incorporate features effecting a water tight seal when secured to the port. Further, the imaging plug 74 incorporates electrical and/or optical components appropriate for delivering a signal or image received from the imaging cable 76 to the image processor 42 (FIG. 1). The imaging cable 76 is appropriately configured for delivering a signal or image received or obtained at the distal tip 54 of the borescope 30 (e.g., a signal generated by the image sensor 32). The imaging plug 74 and corresponding cable 76 are configured to be repeatedly sterilizable as described above.

The bifurcation joint 78 is configured to establish a water tight seal between the illumination cable 72 and the lumen of the borescope 30, and between the imaging cable 76 and the lumen of the borescope 30. As reflected by FIG. 2, in some embodiments, the cables 72, 76 are effectively fixed relative to one another at the bifurcation joint 78. In some embodiments, the bifurcation joint 78 is formed of a polymeric material, such as a thermoplastic polymer including, but not limited to, a polyetherimide (PEI) material available from Saudi Basic Industries Corp. under the trade name ULTEM®. Other materials or constructions appropriate for establishing a water tight seal and repeatable sterilization are also acceptable.

The strain relief body 80 serves as a transition between the bifurcation joint 78 and the borescope 30, and is configured to promote articulation of the borescope 40 relative to the bifurcation joint 78 and the cables 72, 76. The strain relief body 80 can assume various forms, and in some embodiments is a polymeric material formed or bonded over (e.g., heat shrink) an exterior of the borescope 30.

Figure 4:
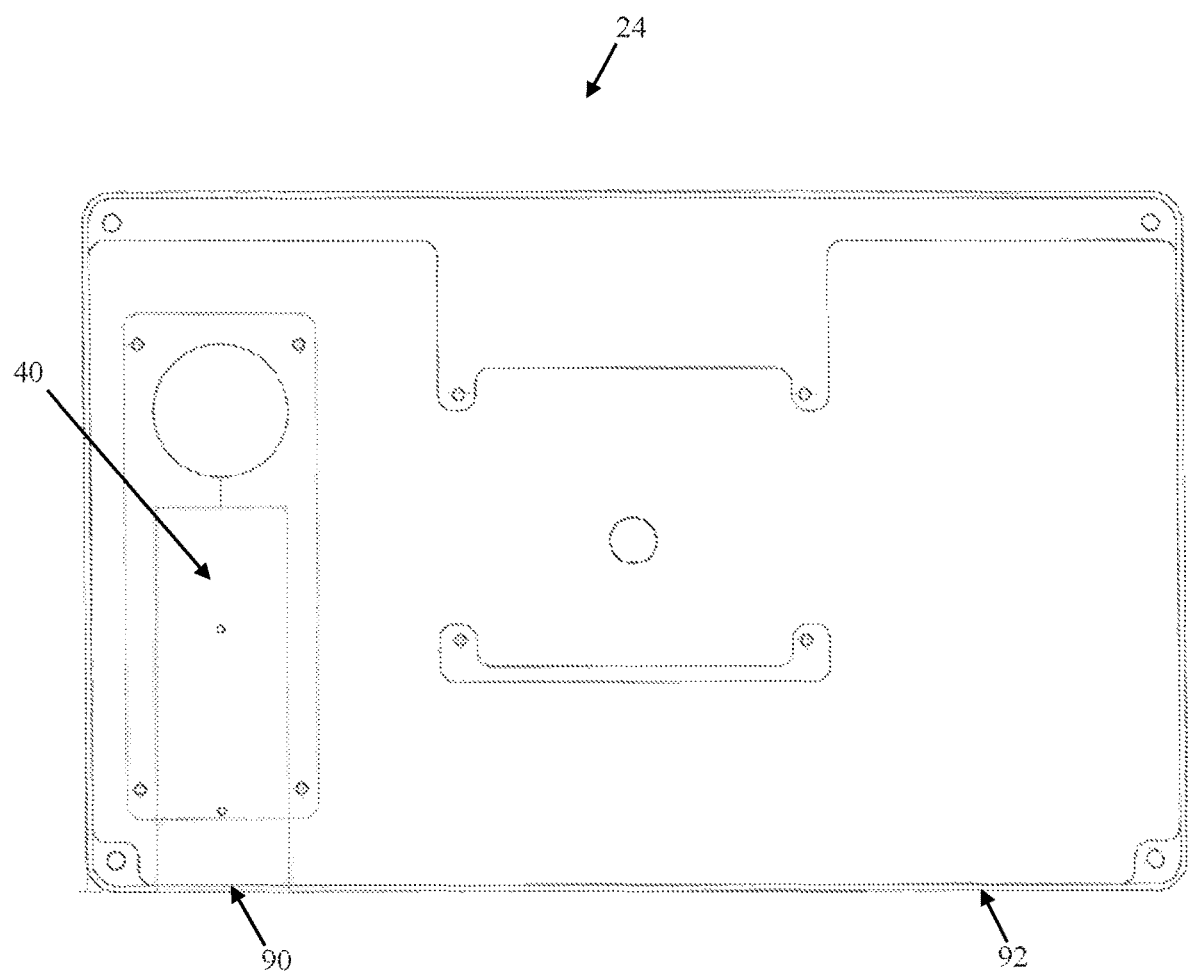
FIG. 4 is a simplified end view of a waterproof housing useful with the inspection system of FIG. 1.

Returning to FIG. 1, the waterproof housing 24 maintains, in some embodiments, the illumination source 40, image processor 42, and the display screen 44. The waterproof features of the housing 24 can be provided in various manners, including selection of materials and/or sealed assembly between various parts. Regardless, and with additional reference to FIG. 4, the housing 24 provides or carries an illumination port 90 and an imaging port 92. The illumination port 90 is electrically and optically connected to the illumination source 40 (represented generally in FIG. 4), and is configured to selectively receive and interface with the illumination plug 70 (FIG. 2), optionally on a water-tight basis. Similarly, the imaging port 92 is electrically connected to the image processor 42, and is configured to selectively receive and interface with the imaging plug 74 (FIG. 2), optionally on a water-tight basis. With this construction, when the illumination plug 70 is connected to the illumination port 90 and the illumination source 40 is activated, light from the illumination source 40 is delivered to the distal tip 54 (FIG. 2) of the borescope 30; and when the imaging plug 74 is connected to the imaging port 92, signals from the image sensor 32 (otherwise representative of an image of an environment at the distal tip 54) are delivered to the image processor 42. When the plugs 70, 74 are disconnected from the corresponding port 90, 92, the borescope assembly 22 is free of connection to the housing 24 and can be thoroughly cleaned and sterilized as described above (e.g., low-temperature, hydrogen peroxide gas plasma sterilized and/or high level disinfected without damaging any components of the borescope assembly 22).

The housing 24 can provide or carry one or more additional components in some embodiments. For example, user interface or actuation devices (e.g., switches, dials, touch screen, etc.) through which a user can operate the inspection system 20 can be provided. Other electrical interfaces can also be included, such as a USB port and appropriate computer processors and/or memory can be provided for delivering or signaling information to a separate device.

With specific reference to FIG. 1, the illumination source 40 can assume a variety of forms appropriate for providing high intensity visible light necessary for normal viewing operation of the borescope 30. In some embodiments, the illumination source 40 is further configured to allow user selection of a desired intensity (e.g., akin to a borescope light source available from SP Concepts under the trade designation INSPEKTOR®, product code 4000). In yet other embodiments, an illumination source is carried by the borescope 30 (e.g., LED lights) such that the separate illumination source 40 (carried by the housing 24) is optional.

Figure 2:
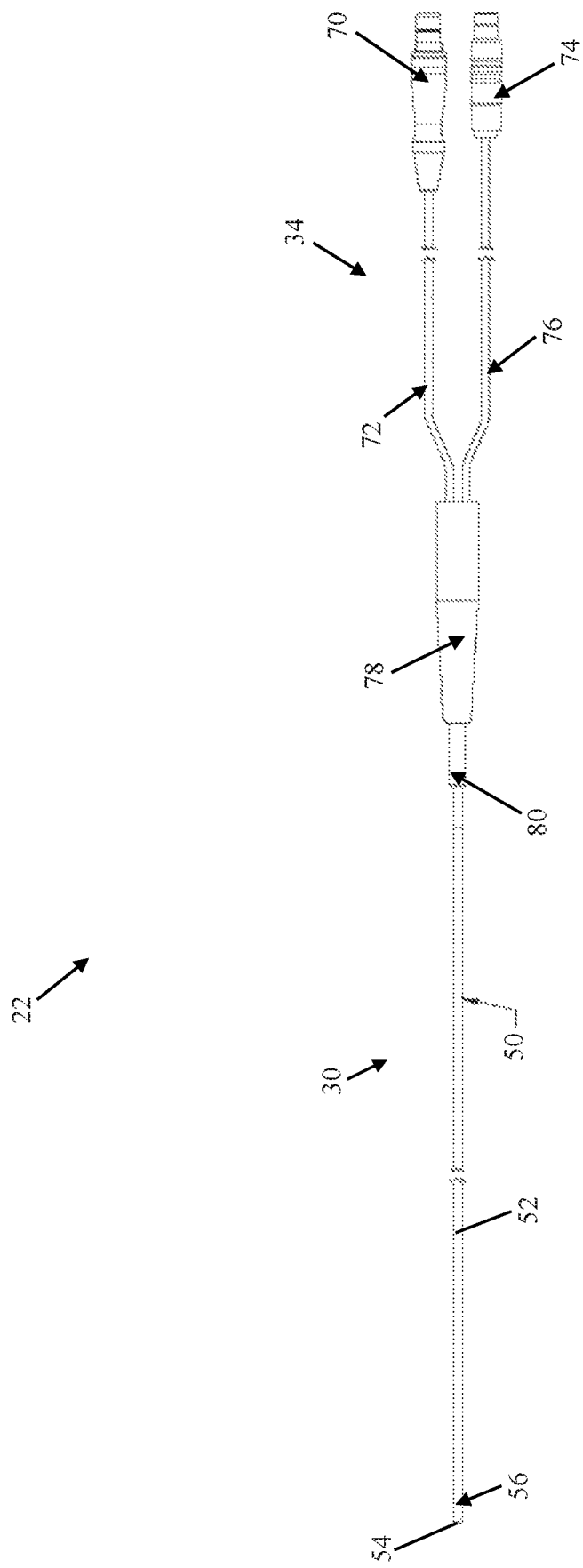
FIG. 2 is a side view of a borescope assembly useful with the inspection system of FIG. 1.

As mentioned above, in some embodiments, the inspection system 20 employs CMOS (complementary metal-oxide-semiconductor)-based imaging technology of a type known in the art. The image sensor 32 can thus be a CMOS sensor (e.g., one chip, three chip, etc.), and the image processor 42 incorporates or operates on software or other programming (e.g., stored in a memory) appropriate for generating images at the display screen 44 from signals generated by the CMOS image sensor 32. The image processor 42 can thus be akin to a CMOS digital camera. Additional camera-type components can also be provided (e.g., lens, mirror, light filters, etc.). Further, the inspection systems 20 can employ other digital camera-type arrangements. For example, the image sensor 32 can be located apart from the borescope 30, with other optical components carried by the borescope 30 being configured to deliver received light (and thus a received image) to the image sensor 32. Other waterproof camera-type arrangements are also envisioned. For example, the waterproof camera provided with the inspection systems of the present disclosure can assume various forms appropriate for optically interfacing with the borescope 30, and in particular for capturing images received at the distal tip 54 (FIG. 2). The camera can be, or can be akin to, a digital camera of a type known in the art (e.g., CMOS, charged coupled device or CCD) with a requisite components for receiving images and electronic components that encode images and videos digitally and optionally stores them for later reproduction. The camera further includes an electrical interface appropriate for connection to the display screen 44 (e.g., a USB port). In some embodiments, the electrical interface may be selectively detachable from the display screen 44. Regardless of exact form, the camera can be rendered waterproof in various manners, such as by a waterproof housing. Similarly, one or both of the borescope 30 and/or the camera can include a component for effectuating a watertight seal between the borescope 30 and the camera (e.g., a gasket).

As mentioned above, in some alternative embodiments of the waterproof borescope assembly 22 not directly reflected by FIG. 1, a waterproof camera is integrally assembled to or permanently carried by the waterproof borescope 30. One non-limiting example of this configuration is a digital camera mounted on the proximal end of the articulating borescope in which image capturing components (e.g., CCD) are carried by the guide tube 50 (FIG. 2). In other embodiments, the borescope 30 can have optical components to which the separately-provided camera is mounted. For example, an eyepiece can be mounted to an imaging end of the guide tube 50. The eyepiece includes one or more optical components that promote visualization of the relayed image (e.g., conventional eyepiece lens). In some embodiments, the eyepiece can have a "focus free" construction. In other embodiments, the eyepiece can include additional components or mechanisms that facilitate user-actuated focusing of a received image. By way of non-limiting example, the waterproof borescope can be a flexible borescope available from SP Concepts of Minneapolis, Minn. under the trade designation INSPEKTOR®, product codes 5001, 5002 and 5003. The eyepiece can alternatively incorporate an opto-electronic or electronic-opto construction.

With alternative embodiments in which a waterproof camera is provided apart from the borescope 30 (any borescope format incorporating the eyepiece as described above), the waterproof camera can assume various forms as known in the art and can be a USB digital camera available from SP Concepts under the trade designation INSPEKTOR®, produce code 3002.

The display screen 44 can assume various forms appropriate for displaying images and video (e.g., digital images and digital video) generated by the image processor 42 (or otherwise delivered from a camera) and in some embodiments is provided as part of a computing device (e.g., a conventional laptop, tablet, or similar computer device programmed (e.g., hardware or software) to interface with the image processor 42; a monitor configured to interface with the image processor 42, etc.). Regardless of exact form, the display screen 44 can be rendered waterproof in various manners, such as by the waterproof case or housing 24.

The support framework 26 can configured to maintain at least one of the borescope assembly 22 and the housing 24 relative to the cleaning station (not shown) during use, and in some embodiments includes an articulating arm (e.g., an articulating arm (or flex arm) available from SP Concepts under the trade designation INSPEKTOR®, product code 6000) configured to mountably receive the borescope 30 (e.g., a clamp or similar mechanism) and flex to allow a user to articulate the mounted borescope 30 to a desired spatial orientation. The framework 26 can further include one or more base components or mechanisms for supporting the articulating arm relative to a surface of the cleaning station. For example, a clamp or mount device can be provided to which the articulating arm is selectively or permanently attached. The base can be configured for temporary connection to a surface of the cleaning station (e.g., a clamp mechanism for clamped attachment to a table edge) or more permanent connection (e.g., a table mount that is affixed to a table top). The support framework 26 can further include, in some optional embodiments, structure(s) for supporting the housing 24, and thus the display screen 44, relative to the cleaning station; these structures can assume any of the formats described above (e.g., articulating arm and base surface mounting component). In some embodiments, the borescope assembly 22 and the housing 24 are commonly supported by the same support framework 26. In other embodiments, the support framework 26 includes a first arm/surface mount structure for supporting the borescope assembly 22 and a second arm/surface mount structure (physically separate from the first arm/surface mount structure) for supporting the housing 24, and thus the display screen 44. Non-limiting examples of components useful as part of the support framework of the present disclosure included the flex arm identified above, along with a scope clamp available from SP Concepts under the trade designation INSPEKTOR®, product code 6001; a table clamp available from SP Concepts under the trade designation INSPEKTOR®, product code 6002; a table mount available from SP Concepts under the trade designation INSPEKTOR®, product code 6004. Regardless of exact form, the support framework 26 can be rendered waterproof in various manners as is known in the art.

Figure 5:
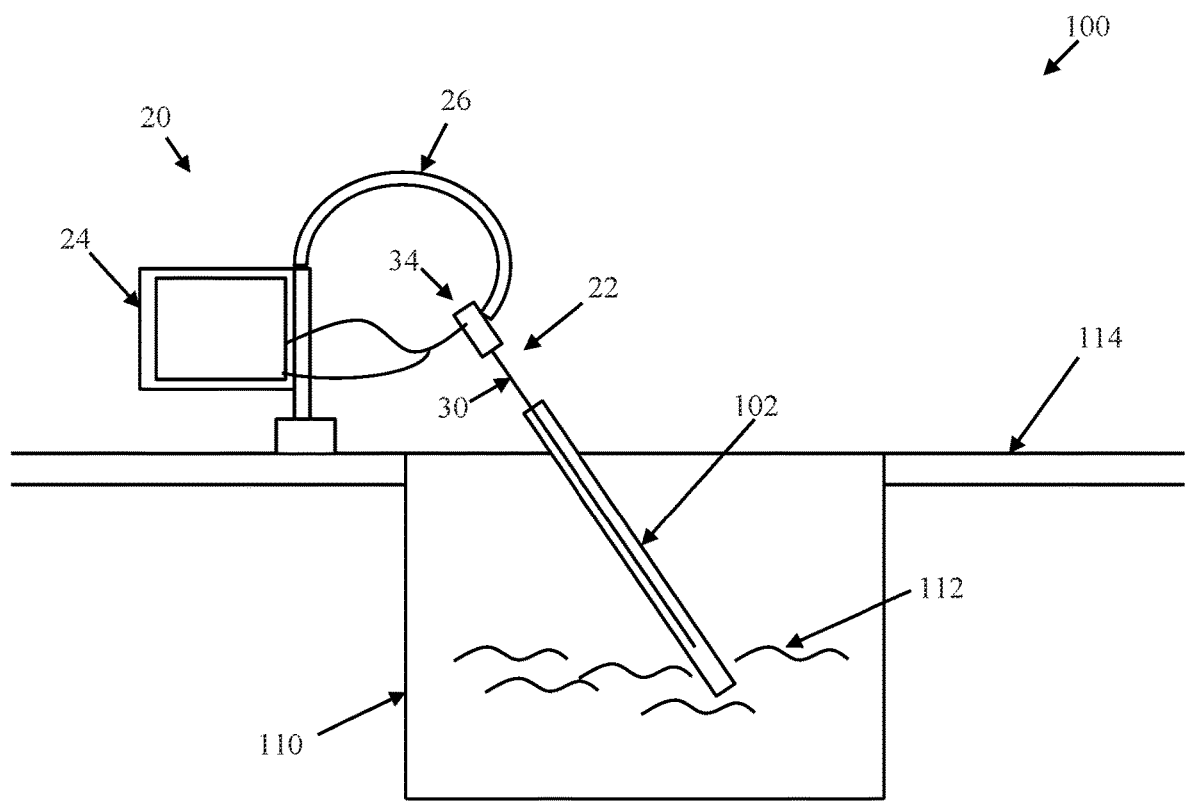
FIG. 5 is a simplified, schematic illustration of an inspection system of the present disclosure arranged in a surgical instrument cleaning station during a cleaning operation.

FIG. 5 schematically reflects one non-limiting example of the inspection system 20 installed at a surgical instrument cleaning station 100 and used for inspecting a surgical instrument 102 during a cleaning process. The cleaning station 100 generally includes a sink 110 maintaining a volume of cleaning liquid 112 (e.g., enzymatic solution, water, etc.). The optional support framework 26 maintains the borescope assembly 22 and/or the housing 24 relative to a surface 114 of the cleaning station 100 (e.g., a table top) in close proximity to the sink 110, and thus in close proximity to the cleaning liquid 112. Due to the waterproof construction, the operator (not shown) can operate the system 20 to visually inspect (and optionally clean or scrub) lumen(s) of the surgical instrument 102 in real time and throughout the cleaning process without concern that the inspection system 20 will become damaged.

Following a cleaning operation as described above, the borescope assembly 22 can be disconnected from the housing 24. Once disconnected, the borescope assembly 22 can be sterilized and high level disinfected (e.g., low-temperature, hydrogen peroxide gas plasma sterilized and/or high level disinfected without damaging any components of the borescope assembly 22). Once sterilized and disinfected, the borescope assembly 22 can be re-used in the performance of another surgical instrument cleaning or inspection operation, followed by sterilization.

Although the present disclosure has been described with reference to preferred embodiments, workers skilled in the art will recognize that changes can be made in form and detail without departing from the spirit and scope of the present disclosure.

What is claimed is:

1. A surgical instrument lumen inspection system for use at a cleaning station, the inspection system comprising:
   a waterproof housing carrying an image processor and carrying a display screen, wherein the image processor is electronically connected to display screen, the housing including an imaging port electronically connected to the image processor; and
   a waterproof borescope assembly including a borescope, an image sensor carried by the borescope, and a connector assembly including an imaging plug configured to selectively connect to the imaging port;
   wherein the borescope assembly is configured to be repeatedly low-temperature, hydrogen peroxide gas plasma sterilized without damaging any components of the borescope assembly;
   and further wherein when the connector assembly is connected to the imaging port, signals generated by the image sensor are delivered to the image processor.

2. The inspection system of claim 1, wherein the borescope assembly is configured to be selectively disconnected from the housing, and to be repeatedly sterilized upon disconnection from the housing.

3. The inspection system of claim 1, wherein the waterproof housing further carries an illumination source and includes an illumination port connected to the illumination source.

4. The inspection system of claim 3, wherein the connector assembly is further configured to selectively connect to the illumination port.

5. The inspection system of claim 4, wherein the connector assembly includes an illumination plug configured to selectively interface with the illumination port.

6. The inspection system of claim 5, wherein the system is configured such that when the imaging plug is disconnected from the imaging port and the illumination plug is disconnected from the illumination port, the borescope assembly is entire free of physical connection with the housing.

7. The inspection system of claim 1, further comprising waterproof support framework configured to maintain the borescope assembly relative to a surface of the cleaning station.

8. The inspection system of claim 7, wherein the support framework is further configured to maintain the housing relative to a surface of the cleaning station.

9. The inspection system of claim 8, wherein the support framework is configured to retain the borescope assembly and the display screen in tandem.

10. The inspection system of claim 1, wherein the borescope includes a guide tube terminating at a distal tip and a cleaning implement projecting from an exterior of the guide tube proximate to the distal tip, the cleaning implement comprising a structure configured to clean surgical residue from internal surfaces of a surgical instrument.

11. The inspection system of claim 10, wherein the cleaning implement is a cloth wipe.

12. The inspection system of claim 1, wherein the image sensor is a complementary metal-oxide-semiconductor (CMOS) sensor.

13. The inspection system of claim 1, wherein a waterproof, sterilizable sheath covering extends along an exterior surface of the borescope.

14. A surgical instrument lumen inspection system for use at a cleaning station, the inspection system comprising:
   a waterproof housing carrying an image processor and carrying a display screen, wherein the image processor is electronically connected to the display screen, the housing including an imaging port electronically connected to the image processor; and
   a waterproof borescope assembly including a borescope, an image sensor carried by the borescope, and a connector assembly including an imaging plug configured to selectively connect to the imaging port;
   wherein the borescope includes a guide tube terminating at a distal tip and a cleaning implement projecting from an exterior of the guide tube proximate to the distal tip, the cleaning implement comprising a structure configured to clean surgical residue from internal surfaces of a surgical instrument;
   and further wherein when the connector assembly is connected to the imaging port, signals generated by the image sensor are delivered to the image processor.

15. The inspection system of claim 14, wherein the cleaning implement is a cloth wipe.

16. The inspection system of claim 14, further comprising waterproof support framework configured to maintain the borescope assembly relative to a surface of the cleaning station.

17. The inspection system of claim 16, wherein the support framework is further configured to maintain the housing relative to a surface of the cleaning station.

18. The inspection system of claim 17, wherein the support framework is configured to retain the borescope assembly and the display screen in tandem.

19. The inspection system of claim 14, wherein a waterproof, sterilizable sheath covering extends along an exterior surface of the borescope.

\* \* \* \* \*